United States Patent
Rich et al.

(10) Patent No.: US 11,728,014 B2
(45) Date of Patent: Aug. 15, 2023

(54) DEEP LEARNING ARCHITECTURE FOR ANALYZING UNSTRUCTURED DATA

(71) Applicant: Flatiron Health, Inc., New York, NY (US)

(72) Inventors: Alexander Rich, Brooklyn, NY (US); Guy Amster, Hoboken, NJ (US); Griffin Adams, Brooklyn, NY (US)

(73) Assignee: Flatiron Health, Inc., New York, NY (US)

( * ) Notice: Subject to any disclaimer, the term of this patent is extended or adjusted under 35 U.S.C. 154(b) by 388 days.

(21) Appl. No.: 16/936,985

(22) Filed: Jul. 23, 2020

(65) Prior Publication Data

US 2021/0027894 A1 Jan. 28, 2021

Related U.S. Application Data

(60) Provisional application No. 63/026,418, filed on May 18, 2020, provisional application No. 62/878,024, filed on Jul. 24, 2019.

(51) Int. Cl.
*G16H 10/60* (2018.01)
*G16H 50/30* (2018.01)
(Continued)

(52) U.S. Cl.
CPC ............. *G16H 10/60* (2018.01); *G06N 3/044* (2023.01); *G06N 7/01* (2023.01); *G16H 50/30* (2018.01)

(58) Field of Classification Search
CPC ...... G16H 50/30; G16H 10/60; G06V 10/768; G06N 3/0445; G06N 7/005
See application file for complete search history.

(56) References Cited

U.S. PATENT DOCUMENTS

2018/0300640 A1 10/2018 Birnbaum et al.
2018/0336183 A1* 11/2018 Lee et al.
(Continued)

OTHER PUBLICATIONS

International Search Report, issued from the European Patent Office in international Application No. PCT/US2020/043255, dated Sep. 28, 2020 (19 pages).

(Continued)

*Primary Examiner* — Michael Tomaszewski
*Assistant Examiner* — William T. Monticello
(74) *Attorney, Agent, or Firm* — Finnegan, Henderson, Farabow, Garrett & Dunner, L.L.P.

(57) ABSTRACT

A model-assisted system for determining probabilities associated with a patient attribute. The processor may be programmed to access a database storing an unstructured medical record associated with a patient and analyze the medical record to identify snippets of information associated with the patient attribute. The processor may generate, based on each snippet, a snippet vector comprising a plurality of snippet vector elements comprising weight values associated with at least one word included in the snippet. The processor may analyze the snippet vectors to generate a summary vector comprising a plurality of summary vector elements, wherein each of the plurality of summary vector elements is associated with a corresponding snippet vector element and is determined based on an analysis of the corresponding snippet vector element. The processor may further generate, based on the summary vector, at least one output indicative of a probability associated with the patient attribute.

26 Claims, 6 Drawing Sheets

(51) Int. Cl.
    *G06N 3/044*     (2023.01)
    *G06N 7/01*     (2023.01)

(56) References Cited

U.S. PATENT DOCUMENTS

| | | | |
|---|---|---|---|
| 2018/0365592 | A1* | 12/2018 | Gu et al. |
| 2019/0065550 | A1* | 1/2019 | Stankiewicz et al. |
| 2020/0218744 | A1* | 7/2020 | Wang et al. |
| 2020/0387572 | A1* | 12/2020 | Allen et al. |
| 2022/0044826 | A1* | 2/2022 | Schaeffer et al. |

OTHER PUBLICATIONS

Sebastien Dubois et al, "Efficient Representations of Clinical Text," ArXiv.org, arXiv:1705.07025, Aug. 20, 2018.

Jeff Mitchell et al, "Vector-based Models of Semantic Composition," Proceedings of ACL-08: HLT, pp. 236-244, Jun. 2008.

Tom Kenter et al, "Siamese CBOW: Optimizing Word Embeddings for Sentence Representations," ArXiv.org, Cornell University Library, Jun. 15, 2016.

Joshua Coates et al. "Frustratingly Easy Meta-Embedding—Computing Meta-Embeddings by Averaging Source Word Embeddings," ArXiv.org. Cornell University Library, Apr. 14, 2016.

Riccardo Miotto et al, "Deep Patient: An Unsupervised Representation to Predict the Future of Patients from the Electronic Health Records", Scientific Reports, vol. 6, No. 1, May 17, 2016.

Benjamin Shickel et al, "Deep EHR: A Survey of Recent Advances in Deep Learning Techniques for Electronic Health Record (EHR) Analysis", ArXiv.org, Cornell University Library, Jun. 12, 2017.

Zexian Zeng et al, "Natural Language Processing for EHR-Based Computational Phenotyping", IEEE/ACM Transactions on Computational Biology and Bioinformatics, New York, NY, vol. 16, No. 1, Jun. 25, 2018.

* cited by examiner

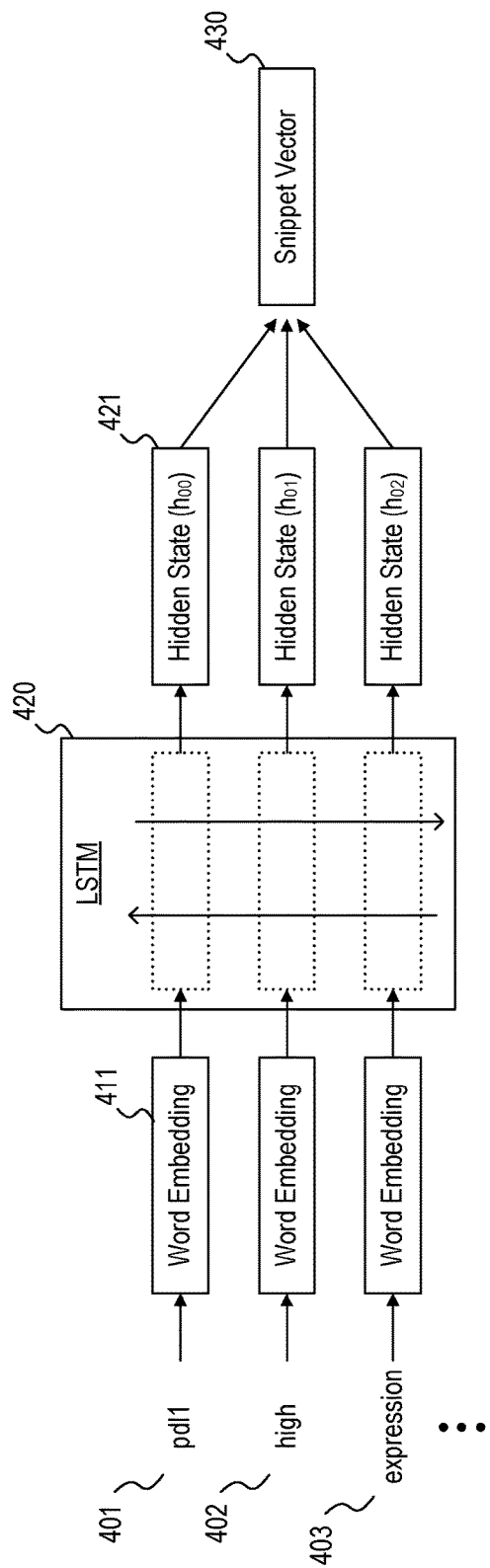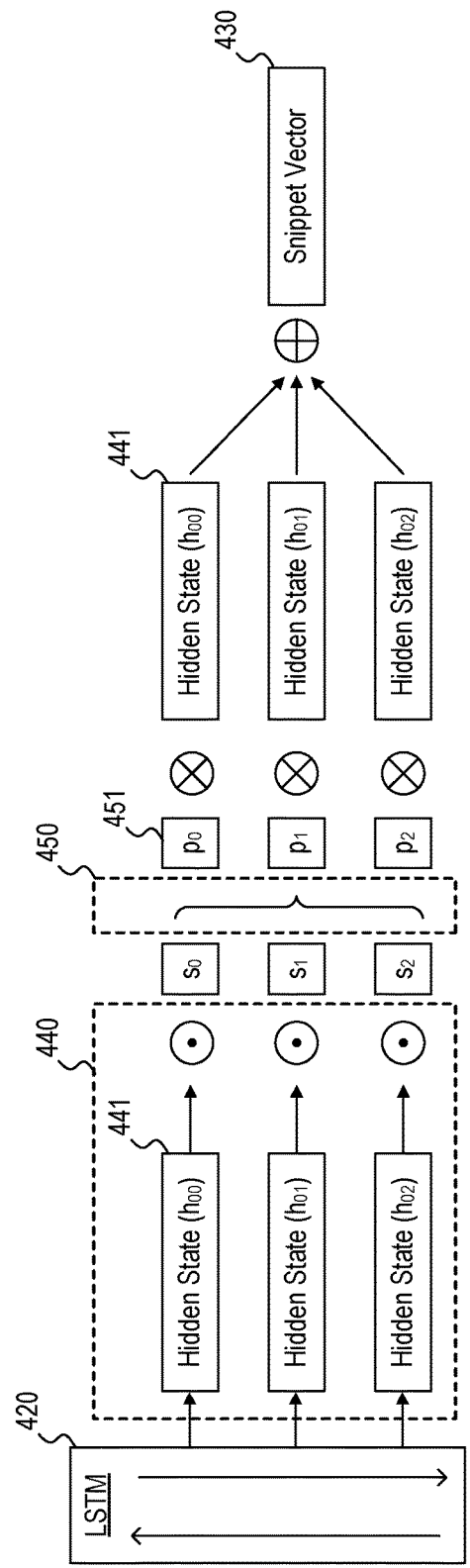
FIG. 4A
FIG. 4B

DEEP LEARNING ARCHITECTURE FOR ANALYZING UNSTRUCTURED DATA

CROSS REFERENCES TO RELATED APPLICATIONS

This application claims the benefit of priority of U.S. Provisional Application No. 62/878,024, filed on Jul. 24, 2019, and U.S. Provisional Application No. 63/026,418, filed on May 18, 2020. The contents of the foregoing applications are incorporated herein by reference in their entirely.

BACKGROUND

Technical Field

The present disclosure relates to identifying representations of attributes in large sets of unstructured data and, more specifically, to the architecture of a deep learning model configured to analyze the data.

Background Information

Information extraction is an increasingly important task that enables software applications to process information from unstructured documents. In many industries, including the medical industry, there are major advantages to processing data at a massive scale. For example, patient medical records, which may contain hundreds of millions of unstructured text documents, often include valuable insights that may be pertinent to treatment of a patient. However, identifying particular attributes exhibited by a patient can be difficult when examining large groups of medical data. For example, this may require searching through thousands of medical documents, each which may include hundreds of pages of unstructured text. Further, due to the nature of the documents, information regarding patient attributes is often represented as handwritten notes or other text which may make automation of this process more difficult.

Some solutions may include developing a machine learning model to determine whether a patient is associated with a particular attribute. For example, the model may be trained based on a set of medical records where it is known whether the patient has been tested for a particular condition or not. But many machine learning techniques are not equipped to process the vast amounts of data required for the medical industry or other industries associated with very large unstructured documents. Many of the information extraction techniques that have been developed are effective on short documents (e.g. product reviews, social media posts, search engine queries) and often do not generalize well to longer documents. For example, a long short-term model (LSTM), or other recurrent neural network, may provide particular advantages when analyzing a series of medical records. However, traditional LSTM neural networks are not effective for this application due to the sheer volume of unstructured text data that must be processed.

Thus, there is a need for an improved approach for identifying patients having particular medical attributes. Solutions should allow for development of a deep learning model architecture that allows for effective information extraction from long documents.

SUMMARY

Embodiments consistent with the present disclosure include systems and methods for determining probabilities associated with a patient attribute. In an embodiment, a model-assisted system may comprise a least one processor. The processor may be programmed to access a database storing at least one unstructured medical record associated with a patient; and analyze the at least one unstructured medical record to identify a plurality of snippets of information in the at least one unstructured medical record associated with the patient attribute. The processor may further be programmed to generate, based on each snippet of the plurality of snippets, a snippet vector comprising a plurality of snippet vector elements, the plurality of snippet vector elements comprising weight values associated with at least one word included in the snippet; and analyze the snippet vectors to generate a summary vector comprising a plurality of summary vector elements, wherein each of the plurality of summary vector elements is associated with a corresponding snippet vector element and is determined based on an analysis of the corresponding snippet vector element. The processor may further be programmed to generate, based on the summary vector, at least one output indicative of a probability associated with the patient attribute.

In another embodiment, a computer-implemented method for determining probabilities associated with a patient attribute. The method may comprise accessing a database storing at least one unstructured medical record; and analyzing the at least one unstructured medical record to identify a plurality of snippets of information in the at least one unstructured medical record associated with the patient attribute. The method may further comprise generating, based on each snippet of the plurality of snippets, a snippet vector comprising a plurality of snippet vector elements, the plurality of snippet vector elements comprising weight values associated with at least one word included in the snippet; and analyzing the snippet vectors to generate a summary vector comprising a plurality of summary vector elements, wherein each of the plurality of summary vector elements is associated with a corresponding snippet vector element and is determined based on an analysis of the corresponding snippet vector element. The method may further comprise generating, based on the summary vector, at least one output indicative of a probability associated with the attribute.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 4A is a block diagram illustrating an example neural network operating on a single snippet, consistent with the disclosed embodiments.

FIG. 4B illustrates an example process for combining hidden states of a neural network model using an attention mechanism, consistent with the disclosed embodiments.

DETAILED DESCRIPTION

Figure 1:
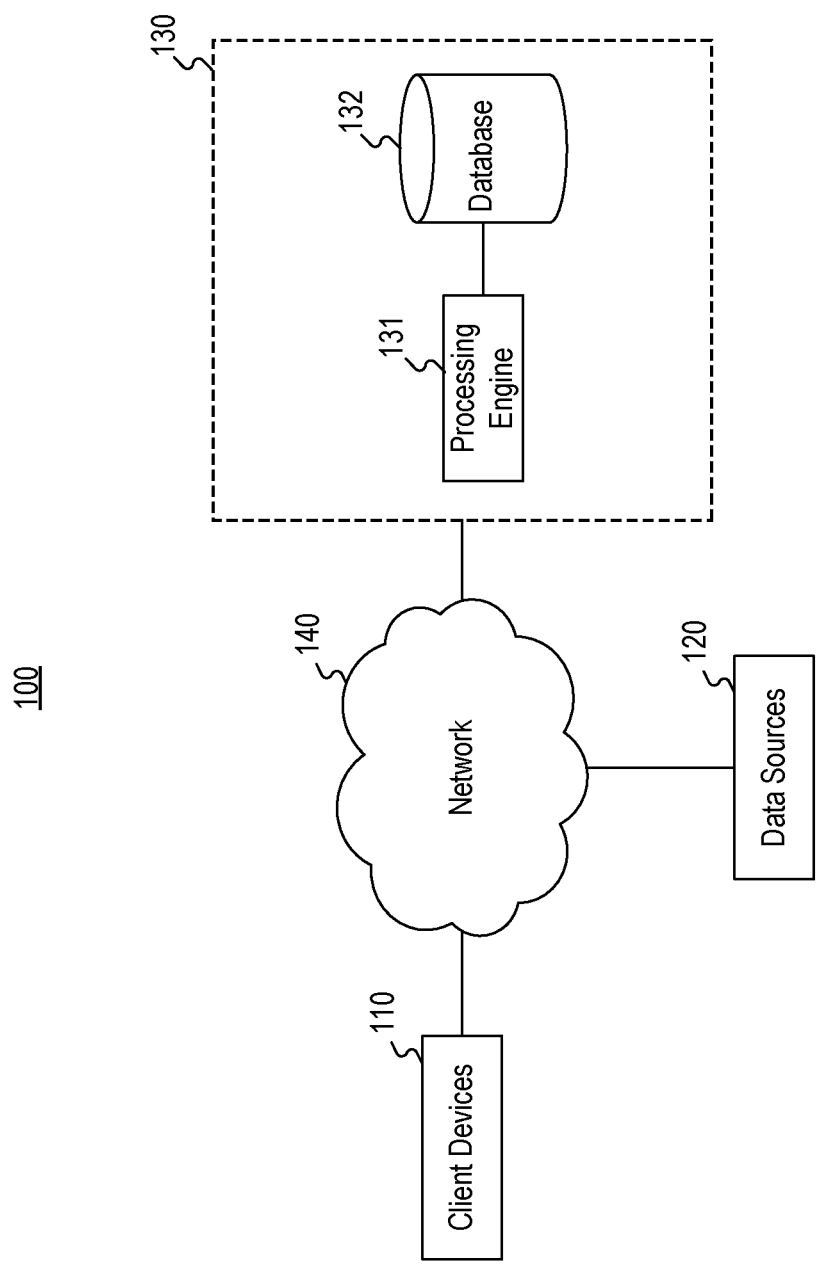
FIG. 1 is a block diagram illustrating an exemplary system environment for implementing embodiments consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Embodiments of the present disclosure provide systems and methods for determining probabilities associated with a patient attribute. A user of the disclosed systems and methods may encompass any individual who may wish to access and/or analyze patient data. Thus, throughout this disclosure, references to a "user" of the disclosed systems and methods may encompass any individual, such as a physician, a researcher, a quality assurance department at a health care institution, and/or any other individual.

FIG. 1 illustrates an exemplary system environment 100 for implementing embodiments consistent with the present disclosure, described in detail below. As shown in FIG. 1, system environment 100 may include several components, including client devices 110, data sources 120, system 130, and/or network 140. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 may include a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processing engine 131 and one or more databases 132, which are illustrated in a region bounded by a dashed line representing system 130. Processing engine 140 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

The components of environment 100 (including system 130, client devices 110, and data sources 120) may communicate with each other or with other components through a network 140. Network 140 may comprise various types of networks, such as the Internet, a wired Wide Area Network (WAN), a wired Local Area Network (LAN), a wireless WAN (e.g., WiMAX), a wireless LAN (e.g., IEEE 802.11, etc.), a mesh network, a mobile/cellular network, an enterprise or private data network, a storage area network, a virtual private network using a public network, a nearfield communications technique (e.g., Bluetooth, infrared, etc.), or various other types of network communications. In some embodiments, the communications may take place across two or more of these forms of networks and protocols.

System 130 may be configured to receive and store the data transmitted over network 140 from various data sources, including data sources 120, process the received data, and transmit data and results based on the processing to client device 110. For example, system 130 may be configured to receive unstructured data from data sources 120 or other sources in network 140. In some embodiments, the unstructured data may include medical information stored in the form of one or more medical records. Each medical record may be associated with a particular patient. Data sources 120 may be associated with a variety of sources of medical information for a patient. For example, data sources 120 may include medical care providers of the patient, such as physicians, nurses, specialists, consultants, hospitals, clinics, and the like. Data sources 120 may also be associated with laboratories such as radiology or other imaging labs, hematology labs, pathology labs, etc. Data sources 120 may also be associated with insurance companies or any other sources of patient data.

System 130 may further communicate with one or more client devices 110 over network 140. For example, system 130 may provide results based on analysis of information from data sources 120 to client device 110. Client device 110 may include any entity or device capable of receiving or transmitting data over network 140. For example, client device 110 may include a computing device, such as a server or a desktop or laptop computer. Client device 110 may also include other devices, such as a mobile device, a tablet, a wearable device (i.e., smart watches, implantable devices, fitness trackers, etc.), a virtual machine, an IoT device, or other various technologies. In some embodiments, client device 110 may transmit queries for information about one or more patients over network 140 to system 130, such as a query for patients having or being associated with a particular attribute, or various other information about a patient.

In some embodiments, system 130 may be configured to analyze patient medical records (or other forms of unstructured data) to identify probabilities of a patient being associated with a particular patient attribute. For example, system 130 may analyze medical records of a patient to determine whether the patient has undergone testing for a particular attribute, identify specific test results associated with the attribute (having been tested positive, negative, etc.), or various other characteristics. System 130 may be configured to use one or more machine learning models to identify these probabilities. As described above, machine learning architectures have been developed for analysis of relatively short documents. These techniques, however, often do not translate well to longer documents, such as patient medical records. For example, the implementation of long short-term memory (LSTM) models and other forms of recurrent neural networks may not be feasible using traditional architectures, due to the volume of text in the unstructured documents.

To overcome these and other limitations, the systems and methods of the present disclosure may parse large data sources into a series of snippet representations. These snippets may be processed individual using a LSTM-based pipeline, or similar neural network model, to learn latent snippet representations, which may be combined and used for classification. To improve the accuracy and efficiency of the model, it may be important extract only relevant text from the data sources for analysis. Accordingly, a regular expression associated with particular patient attribute may be used to extract relevant snippets from the data sources. Further, a particular model architecture may be implemented to effectively learn from these extracted snippets. These processes are described in detail below.

While patient medical records are used as an illustrative example throughout the present disclosure, it is understood that in some embodiments, the disclosed systems, methods, and/or techniques may similarly be used for identifying other types of individuals, objects, entities, etc. based on other forms of large unstructured data source. Accordingly, the disclosed embodiments are not limited to analysis of medical records. For example, similar techniques may be applied to legal documents, employee records, criminal or law enforcement databases, government (e.g., state, federal, or local) databases, transportation records (e.g., shipment records, etc.), educational institution records, public records, or various other data sources that may include extensive unstructured data.

Figure 2:
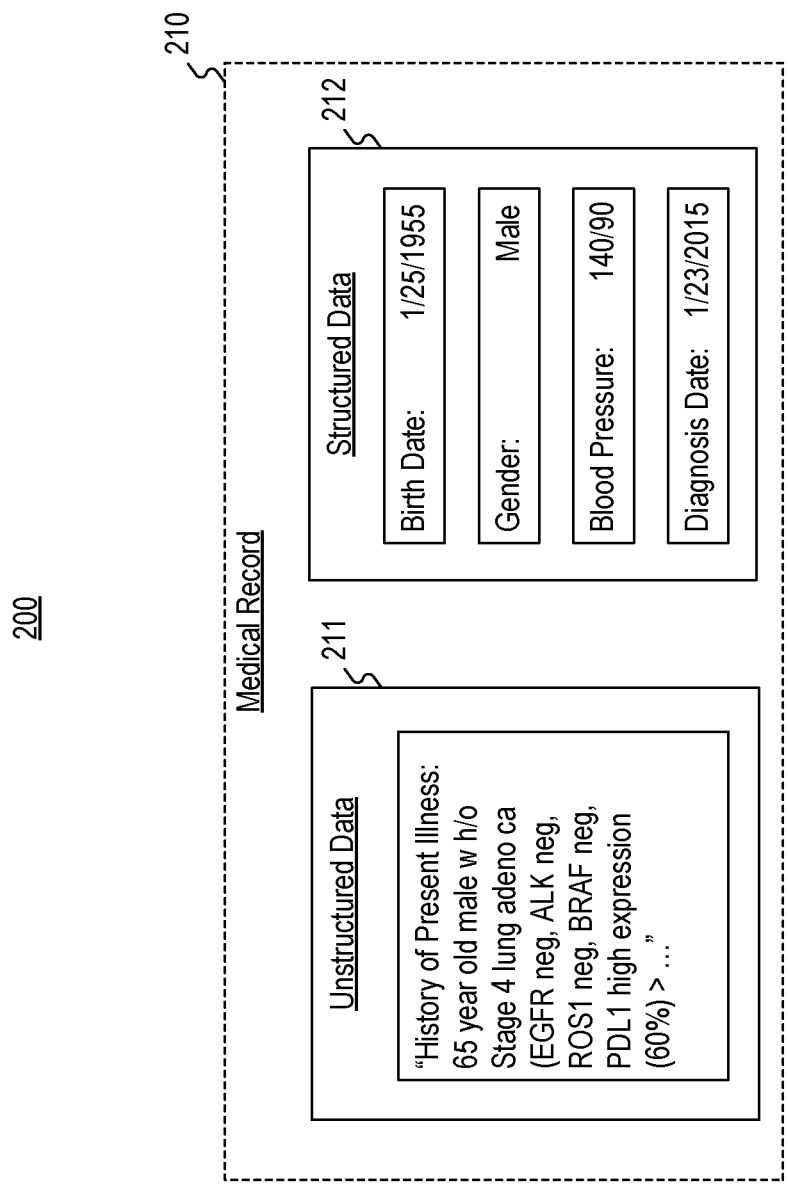
FIG. 2 is a block diagram illustrating an exemplary medical record for a patient, consistent with the disclosed embodiments.

FIG. 2 illustrates an exemplary medical record 200 for a patient. Medical record 200 may be received from data sources 120 and processed by system 130 to identify whether a patient is associated with particular attributes, as described above. The records received from data sources 120 (or elsewhere) may include both structured data 210 and unstructured data 220, as shown in FIG. 2. Structured data 210 may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient. Unstructured data may include information about the patient that is not quantifiable or easily classified, such as physician's notes or the patient's lab reports. Unstructured data 220 may include information such as a physician's description of a treatment plan, notes describing what happened at a visit, statements or accounts from a patient, subjective evaluations or descriptions of a patient's well-being, radiology reports, pathology reports, etc.

In the data received from data sources 120, each patient may be represented by one or more records generated by one or more health care professionals or by the patient. For example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases. In some embodiments, the records may be stored and/or provided a plurality of electronic data representations. For example, the patient records may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process. In some embodiments, the unstructured data may be captured by an abstraction process, while the structured data may be entered by the health care professional or calculated using algorithms.

In some embodiments, the unstructured data may include data associated with particular patient attributes. As an illustrative example, the patient attribute may comprise a smoking status for a patient. In this example, system 130 may analyze a patient medical records to determine whether the patient is a smoker. For example, unstructured data 211 may include notes (e.g., from a physician, a nurse, a lab technician, etc.) indicating that the patient smokes a certain number of packs of cigarettes per week, that the patient uses an electronic cigarette, or similar notes. In another embodiment, system 130 may analyze the patient medical records to determine whether a patient has been tested for a particular indicator, such as the programmed death-ligand 1 (PDL1) protein. For example, the unstructured data may include notes (e.g., from a physician, a nurse, a lab technician, etc.) discussing PDL1 test results (e.g., whether the patient has been tested for PDL1, results of the test, analysis of the results, etc.). While patient identification based on a PDL1 testing status and/or smoking history is used throughout the present disclosure, this is by way of example. It is understood that the disclosed systems, methods, and/or techniques may similarly be used for other means of identifying patients (e.g., whether a patient has been prescribed a particular drug, whether the patient has received a particular treatment, etc.).

Figure 3A:
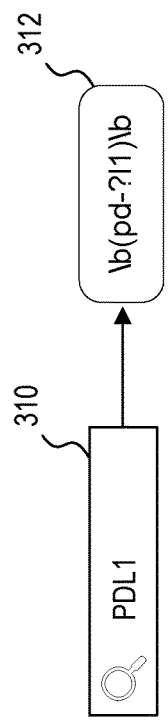
FIG. 3A illustrates an example keyword that may be used to search for a patient attribute, consistent with the disclosed embodiments.

As discussed above, system 130 may analyze the unstructured medical records to extract snippets of text from the unstructured data of the medical records. As used herein, a snippet may refer to a relatively small portion of text or other data contained within a larger document. A snippet may include a portion of text surrounding and including information relevant to a particular patient attribute. To identify the snippets, system 130 may perform a keyword search to find locations in a document where the relevant attribute is discussed. FIG. 3A illustrates an example keyword 312 that may be used to search for a patient attribute, consistent with the disclosed embodiments. In the example shown in FIG. 3A, system 130 may be configured to determine whether a patient associated with a set of medical records has been tested for the PDL1 protein and/or the results of the test. Accordingly, a search term 310 may include text "PDL1."

In some embodiments, system 130 may perform a keyword search for the term "PDL1." In some instances, however, PDL1 testing and the test results may be discussed using alternate notations. For example, in some instances the term may include a dash and may be expressed as "PD-L1". To avoid missing snippets of text including these alternate representations, a keyword search may be performed using regular expression or "regex" 312. A regular expression may include any sequence of characters defining a search pattern. For searches for PDL1 testing, regular expression 312 may comprise the term "\b(pd-?l1)\b," where "-?" is a variable element to include instances where a dash is and is not included. The term "\b" may represent a word boundary, allowing system 130 to search for whole word matches of the term.

In some embodiments, more complex regular expressions may be used. For example, regular expression 312 may include a more permissive regex such as "\b(p\W{0,2}d\W{0,2}[1lit]\W{0, 2} [1lit])\b," which may account for additional characters and potential errors due to optical character recognition (OCR) from scanned documents. Regular expression 312 may be generated automatically by system 130, for example, by adding word boundary terms to the search term, including variable elements at various locations associated with the search term, etc. In other embodiments, regular expression 312 may be developed and input by a user into system 130. It is understood that the search term and regular expressions described above are provided by way of example. Various other search terms, regular expressions, and/or regular expression formats may be used.

In addition to regular expression 312, system 130 may search for snippets using other target terms that may be associated with the patient attribute. For example, where the patient attribute includes PDL1 testing, target terms such as "high expression," "low expression," "tumor proportion score," "tps," "staining," and "insufficient" may commonly be associated with PDL1 testing and may also be used to perform searches on the unstructured documents. Similarly, where the patient attribute is a smoking status of the patient, target terms may include, for example, "cigarette(s)," "packet(s)," "cigar(s)," "smoke(r\s\d)," "chew(s)," "smoking," "ppd," "nicotine," "pipe," "tobacco," "snuff," "marijuana," "smokeless," "chewing," and "smoker." Regular expressions based on these target terms may also be used, similar to regular expression 312. Because these terms are broader, they may be used in relation to other traits than the particular patient attribute being searched for. For example, the term "staining" may be used in many other contexts besides PDL1 testing. To avoid returning irrelevant snippets, the additional target terms may be used to extract snippets only from documents pertinent to the patient attribute. For example, system 130 may first perform a search using regular expression 312 to find documents including discussions of PDL1 testing and may extract snippets based on the additional target terms only from those documents. The use of these target terms may ensure that relevant snippets that do not include regular expression 312 are still identified and analyzed by system 130.

Figure 3B:
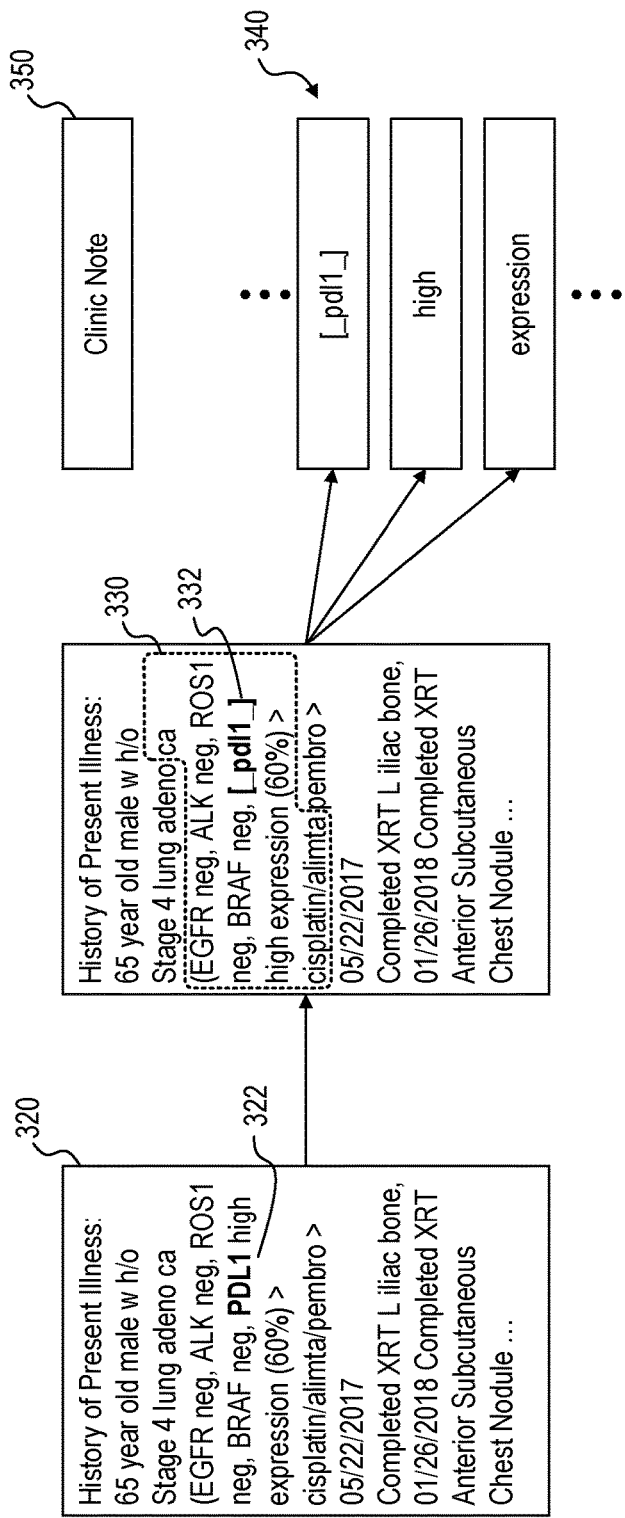
FIG. 3B illustrates an example snippet that may be extracted from a document, consistent with the disclosed embodiments.

The search process described above may be performed on each of the unstructured documents to extract snippets associated with the patient attribute. FIG. 3B illustrates an example snippet 330 that may be extracted from a document, consistent with the disclosed embodiments. Based on regular expression 312, system 130 may identify a document 320 including a target token 322 representing an instance of the search term within the text. System 130 may then extract a snippet of text surrounding target token 322, as shown in FIG. 3B by snippet 330. In some embodiments, snippet 330 may be defined based on a predefined window. For example, the snippet may be defined based on a predetermined number of characters before and after target token 322 in the text (e.g., 20 characters, 50 characters, 60 characters, or any suitable number of characters to capture context for use of the term). The window may also be defined to respect word boundaries such that partial words are not included in the edges of the snippet, for example, by expanding or narrowing the window to end at word boundaries. In some embodiments, the window may be defined based on a predefined number of words, or other variables.

In some embodiments, system 130 may replace target token 322 with a placeholder 332. This may ensure that the patient attribute is expressed using the same terminology in each of the extracted snippets. For example, documents including "PDL1" and documents including "PD-L1" may both result in extracted snippets including the term "[pdl1_]," as illustrated in FIG. 3B. The use of a placeholder may also improve performance of a machine learning model by reducing feature sparsity, speeding up training time, and allowing the model to converge with more limited sets of labeled data.

Snippet 330 may then be sanitized to remove non-substantive text from the snippet. Non-substantive text may include, for example, HTML tags, dates, pagination, or other data not relevant to discussion of the patient attribute. The non-substantive text may be identified using a custom set of regular expression filters configured to identify common formats of non-substantive text. For example, one or more regular expression filters may be designed to search for text of the format MM/DD/YYYY (or other variations) and other common date formats and remove this text from the snippet. Many punctuation characters may also be removed, however, system 130 may be configured to retain some punctuation that may be relevant to the patient attribute (e.g., "+," "−," etc.). A list of potentially relevant punctuation marks may be maintained in a database (e.g., database 132). The list may be a universal list applicable to many patient attributes, or may be developed in association with the particular attribute being examined.

System 130 may also tokenize snippet 330 to split the raw text into a plurality of tokens, such as tokens 340 shown in FIG. 3B. The tokens may be split according to word boundaries identified in the text, such that each token includes a word within the snippet. For example, beginning with placeholder 332, system 130 may extract tokens "[_pdl1_]," "high," and "expression" from snippet 330. Tokens may be extracted in both directions from placeholder 332 and throughout the full snippet 330. In some embodiments, the tokens may comprise single words, as shown in FIG. 3B. In other embodiments, the tokens may be configured to include multiple words. For example, tokens associated with the term "BRAF neg" may be generated as "neg," "BRAF neg," and "BRAF." The present disclosure is not limited to any particular form or format of tokens extracted from the snippets. In addition to the tokenization, system 130 may also extract a document category 350 associated with document 320. For example, document category 350 may indicate whether document 320 is a clinic note, a pathology report, or another common document type. Document category 350 may be identified within the document itself (e.g., within metadata or tags associated with document 320, a filename of document 320, etc.), or may be determined through analysis of the text of document 320 (e.g., based on document format, keywords included in the document, etc.).

The process described above with respect to FIG. 3B may be repeated for each instance of regular expression 312 or additional target terms identified in the text to extract a plurality of snippets from the unstructured documents. Each of the snippets may be tokenized as described above. The extracted snippets may then be fed into a deep learning model architecture to identify probabilities for the patient associated with the patient attribute.

In some embodiments, two or more of the generated snippets may be the same or very similar due to repeated text within the unstructured data. For example, in doctor office records or other longitudinal patient data, text from previous visits may be copied and pasted, and thus may appear multiple times in the same record. To eliminate this redundancy, system 130 may remove duplicate snippets. In some instances, some, but not all of the text may be duplicative in the record and therefore, even though the snippet is not identical to another snippet, it may nevertheless be redundant. To account for this, system 130 may implement an overlap-based metric to measure snippet similarity. For example, a greedy algorithm may be employed, in which system 130 loops through snippets and adds a snippet only if its words are not covered by another snippet based on a predefined percentage. The amount of coverage may be defined as amount of word overlap between two snippets divided by the length of the snippet being analyzed. For example, a candidate snippet may be included only if at least 80% of the words of the candidate snippet are not already included in another snippet. Various other coverage percentages may be used.

The model architecture may first operate on each snippet in parallel, before integrating this information to create a prediction for the patient as a whole. FIG. 4A is a block diagram illustrating an example neural network operating on a single snippet, consistent with the disclosed embodiments. The snippet may include a plurality of tokens 401, 402, and 403 which may have been identified through the tokenization process described above. For example, tokens 401, 402, and 403 may correspond to tokens 340 shown in FIG. 3B. Each of the tokens may be converted into a word embedding before being passed through a neural network. For example, token 401 may be converted to word embedding 411. Word embedding 411 may be a representation of token 401 mapped to a vector of real numbers having a predefined dimension. For example, a dimension of 128 values may be used, however, word embedding 411 may have any suitable dimension. Word embedding 411 may be determined based on a training set of data. System 130 may build a vocabulary including all of the tokens represented in the extracted snippets in the training data. These tokens may be indexed and projected into an embedding space. Token 411 may then be converted to word embedding 411 defined by the learned word embedding.

Next, word embedding 411 may be passed through a recurrent neural network, such as LSTM 420. In some embodiments, LSTM may include a bi-directional LSTM. The LSTM may have a hidden dimension corresponding to the word embedding, which, consistent with the example above, may include a hidden dimension of 128. LSTM 420 may be trained to generate final hidden states including weight values based on the input tokens. For example, LSTM 420 may be trained based on a training data set of snippet tokens with known outcomes (such as whether the patient is associated with the patient attribute). A final hidden state 421 may be generated as a result of the forward and backward passes of the bi-directional LSTM. The same process may be performed across all snippet tokens 401-403 and these final hidden states may be combined to form a snippet vector 430.

In some embodiments, snippet vector 430 may be a concatenation of the final hidden states. For example, snippet vector 430 may comprise a concatenation of hidden states $h_{o0}$, $h_{o1}$, and $h_{o2}$. Various other means for combining the hidden states to form snippet vector 430 may be used. FIG. 4B illustrates an example process for combining hidden states of a neural network model using an attention mechanism, consistent with the disclosed embodiments. At each timestep of LSTM 420, system 130 may take a weighted average of the hidden states. The weights may be calculated by taking a dot product of each intermediate hidden state vector 441 with a learned attention weight vector, as shown in operation 440. The attention weight vector may be learned as part of a training process for LSTM 420. A softmax operation 450 may be used to convert the dot product outputs for each hidden state vector 441 into proportions, such as proportion 451. Snippet vector 430 may be determined based on a weighted combination of all of the hidden states according to the proportions. Notably, this process may be performed for all intermediate hidden states generated by LSTM 420. Accordingly, LSTM 420 may directly pass information from any intermediate hidden state into the full snippet vector representation.

In some embodiments, the initial hidden state of LSTM 420 may be encoded with snippet metadata to improve the model. For example, LSTM 420 may be hot encoded with a category of the snippet (e.g., indicated by document category 350) and a target term the snippet was extracted based on (e.g., PDL1, etc.). In other words, rather than initializing the LSTM with a vector of zeros before proceeding to the first (or last token), the LSTM model may be initialized with a one-hot encoding of the snippet metadata. By providing context of the snippet in an initial state, it may be handled differently by the LSTM and may improve the results of the model.

The processes shown in FIGS. 4A and 4B are provided by way of example. It is understood that various other suitable methods for compiling a resulting snippet vector from the hidden states generated in LSTM may be used. Further, the LSTM 420 is provided by way of example. For example, LSTM 420 may be single- or multi-layered, may be single- or bi-directional, etc. Other forms of recurrent neural networks may also be used to generate snippet vector 430.

The process described above with respect to FIGS. 4A and 4B may be repeated for each snippet extracted from the unstructured data, resulting in a plurality of snippet vectors. To determine probabilities associated with the patient attribute, it may be necessary to reduce the sequence of snippet vectors to a single summary vector before classification.

Figure 5:
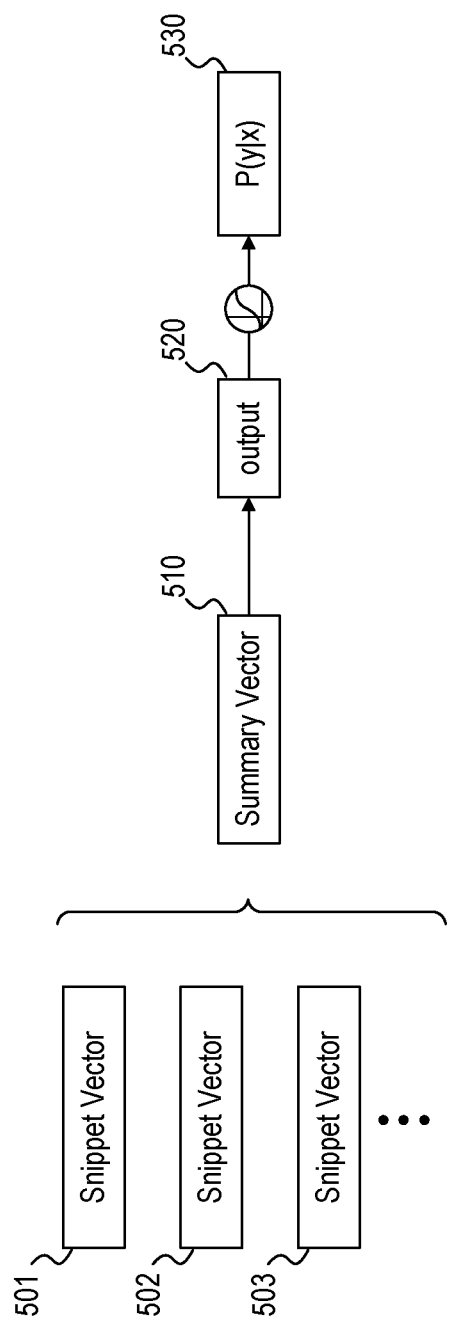
FIG. 5 is a block diagram illustrating an example process for generating a summary vector and probabilities based on a plurality of snippet vectors, consistent with the disclosed embodiments.

FIG. 5 is a block diagram illustrating an example process for generating a summary vector 510 and probabilities 530 based on a plurality of snippet vectors, consistent with the disclosed embodiments. One or more snippet vectors 501, 502, and 503 may be generated based on associated input snippets using a trained neural network, as described above. Snippet vectors 501, 502, and 503 may be reduced to a single summary vector 510. As an example, each of snippet vectors 501, 502, and 503 may contain 128 elements (or any suitable number of elements defined by the neural network model), and summary vector 510 may similarly contain 128 elements. In some embodiments, summary vector 510 may be determined based on an element-wise function performed on snippet vectors 501, 502, and 503. For example, summary vector 510 may be determined using an element-wise max operation performed across the snippet vectors such that each element of summary vector 510 comprises a maximum of corresponding elements in snippet vectors snippet vectors 501, 502, and 503. For example, the first element of summary vector 510 may be a maximum value of the first element of snippet vector 501, the first element of snippet vector 502, and he first element of snippet vector 503. Similarly, the second element of summary vector 510 may be a maximum value of the second element of snippet vector 501, the second element of snippet vector 502, and the second element snippet vector 503. This may be repeated for each element position to define summary vector 510. Various other operations may be used to define summary vector 510, including an element-wise minimum operation, an element-wise average operation, or the like.

System 130 may be trained to project summary vector 510 onto an output space 520 in a feed-forward layer. Finally, a softmax layer may be used to create a predicted probability 530 for each output class. Predicted probabilities 530 may be converted into predicted class labels. The number and type of probabilities determined using summary vector 510 may depend on the type of patient attribute being analyzed. For example, if PDL1 status is used as the patient attribute, the probabilities may include a probability the patient has tested positive for PDL1, a probability the patient has tested negative for PDL1, a probability the patient has not been tested, and a probability the result is indeterminate. Similarly, if the patient attribute is a smoking status of the patient, the probabilities may include a probability the patient has a history of smoking, a probability the patient has no history of smoking, and a probability that the result is indeterminate. Various other probabilities may be included depending on the type of patient attribute being analyzed. Each probability may be expressed in a variety of formats. For example, the probabilities may be expressed as a percentage, on a predefined scale (e.g., 1-10, 1-5, etc.), as a list of predefined classifications (e.g., "high probability," "low probability," etc.), or any other suitable forms.

The resulting probabilities may indicate whether the patient is associated with the patient attribute. For example, the probabilities may indicate a whether a patient has been tested for PDL1 and the results of that test, with associated levels of confidence. Accordingly, system 130 may be used for classifying patients based on unstructured medical data within a patient's medical records. Because only relevant snippets of each document are analyzed, system 130 may advantageously use a LSTM model for determining the probabilities associated with the patient attribute, despite the relatively large documents commonly included in patient medical records.

Figure 6:
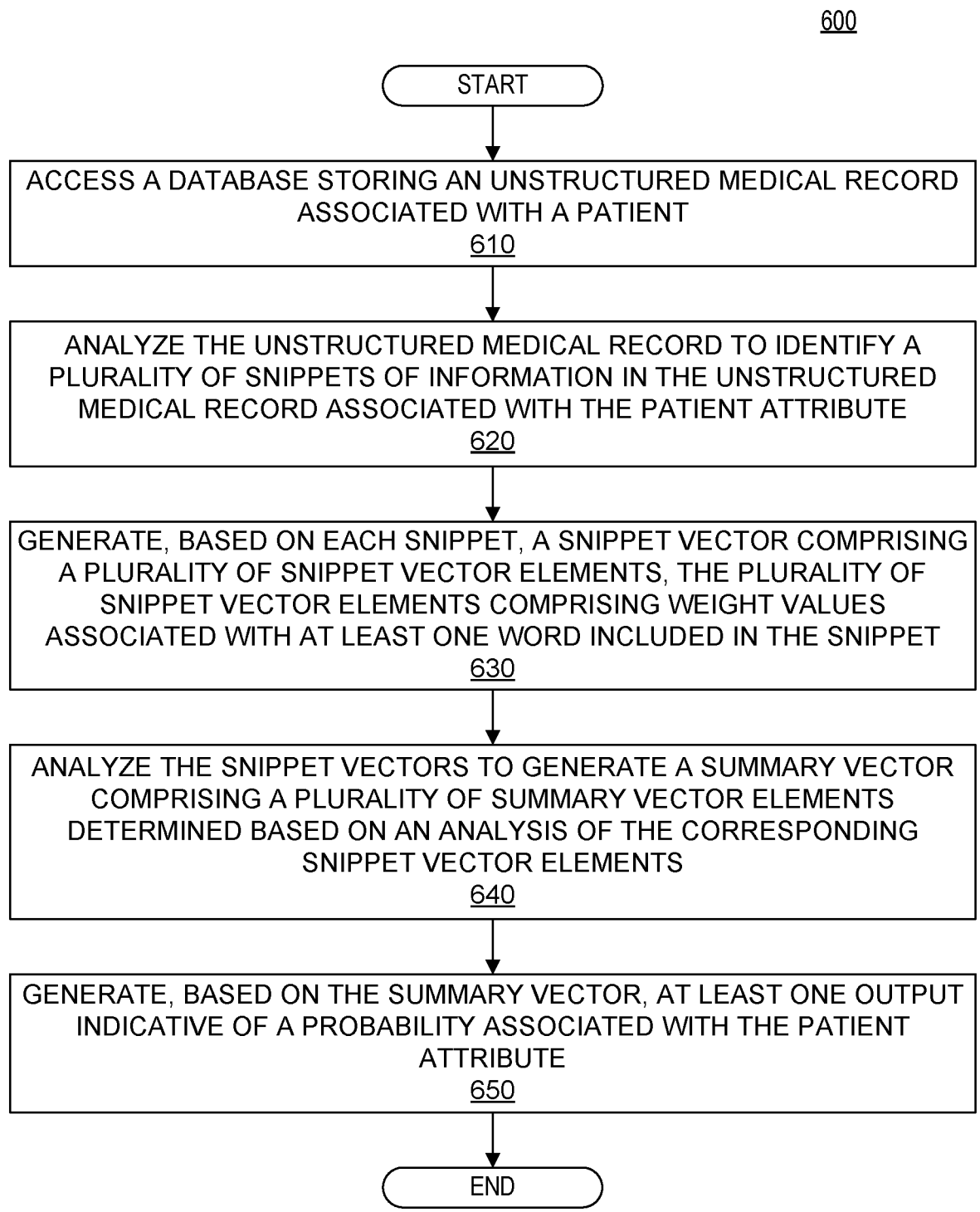
FIG. 6 is a flowchart showing an example process for determining probabilities associated with an attribute, consistent with the disclosed embodiments.

FIG. 6 is a flowchart showing an example process 600 for determining probabilities associated with an attribute, consistent with the disclosed embodiments. Process 600 may be performed by at least one processing device, such as processing engine 131, as described above. It is to be understood that throughout the present disclosure, the term "processor" is used as a shorthand for "at least one processor." In other words, a processor may include one or more structures that perform logic operations whether such structures are collocated, connected, or disbursed. In some embodiments, a non-transitory computer readable medium may contain instructions that when executed by a processor cause the processor to perform process 600. Further, process 600 is not necessarily limited to the steps shown in FIG. 6, and any steps or processes of the various embodiments described throughout the present disclosure may also be included in process 600, including those described above with respect to FIGS. 3A-5.

In step 610, process 600 may include accessing a database storing at least one unstructured medical record. For example, system 130 may access patient medical records from local database 132 or from an external data source, such as data sources 120. The medical record may comprise one or more electronic files, such as text files, image files, PDF files, XLM files, YAML files, or the like. The at least one unstructured medical record may correspond to medical record 210 discussed above. For example, the unstructured medical record may contain at least some unstructured data 211. The unstructured information may include text written by a health care provider, a radiology report, a pathology report, or various other forms of text associated with the patient. In some embodiments the medical record may further include additional structured data 212.

In step 620, process 600 may include analyzing the at least one unstructured medical record to identify a plurality of snippets of information in the at least one unstructured medical record associated with the patient attribute. In some embodiments, identifying the snippets may comprise searching the at least one unstructured medical record for a keyword associated with the patient attribute. For example, the patient attribute may include whether the patient has been tested for PDL1, and the keyword may comprise the text "PDL1." In some embodiments, the keyword may comprise at least one variable element. For example, the keyword may be expressed using a regular expression, such as regular expression 312. Accordingly, the keyword may account for alternative spellings of the patient attribute, additional or extraneous characters appearing in the text, errors due to OCR processing of scanned documents, word boundaries, and other variables that may affect snippet extraction.

In some embodiments, additional snippets may be identified based on target terms associated with the keyword. For example, where the patient attribute is a smoking history of the patient, target terms including "cigarette," "packs," "vaping," or other terms related to smoking may be included. To avoid irrelevant snippets from being identified, snippets based on these target terms may be extracted only from documents including the keyword in an initial search. Further, in some embodiments, one or more redundant snippets may be removed if a number of words covered by another snippet (or percentage of words) exceeds a predetermined threshold. While step 620 is described based on a single snippet, it is understood that the same process may be performed on multiple snippets extracted from the unstructured medical record.

In step 630, process 600 may include generating, based on each snippet of the plurality of snippets, a snippet vector comprising a plurality of snippet vector elements. The plurality of snippet vector elements may comprise weight values associated with at least one word included in the snippet. In some embodiments, the snippet vector may be generated using a neural network, such as a long short-term memory network, or other form of recurrent neural network. For example, a snippet including tokens 401, 402, and 403 may be passed through LSTM 420 to generate snippet vector 430. Accordingly, step 630 may include combining a plurality of hidden states to form snippet vector 430. This may include a concatenation, an attention mechanism, or various other means for generating a snippet vector, as described above with respect to FIGS. 4A and 4B.

In step 640, process 600 may include analyzing the snippet vectors to generate a summary vector comprising a plurality of summary vector elements. For example, snippet vectors 501, 502, and 503 may be reduced to a single snippet vector 510. Each of the plurality of summary vector elements may be associated with a corresponding snippet vector element. For example, the snippet vector(s) and the summary vector may each comprise the same number of elements, such that there is a corresponding element in the snippet vector(s) for each element of the summary vector. Further, each of the plurality of summary vector elements may be determined based on an analysis of the corresponding snippet vector element. For example, each summary vector element may comprise a maximum of corresponding snippet vector elements in a plurality of snippet vectors (e.g., using an element-wise maximum operation), as described above.

In step 650, process 600 may include generating, based on the summary vector, at least one output indicative of a probability associated with the attribute. In some embodiments, the probability may comprise a probability of whether a test has been performed on the patient associated with the patient attribute. For example, the probability comprises a probability of whether the patient has been tested for PDL1. Additionally, or alternatively, probability may comprise a probability of whether the patient has tested positive (or negative) for the patient attribute. For example, the probability may comprise a probability of whether the patient has tested positive for PDL1. In other embodiments, the probability may comprise a probability of a patient exhibiting a particular health-related trait. For example, the probability may comprise a probability of whether the patient has a history of smoking. In some embodiments, the output may include an indication that an association between the patient and the patient attribute is indeterminate. For example, the output may include a probability that the correlation between the patient and that patient attribute cannot be determined based on the unstructured medical record.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A model-assisted system for determining probabilities associated with a patient attribute, the system comprising:
at least one processor programmed to:
  access a database storing at least one unstructured medical record associated with a patient;
  analyze the at least one unstructured medical record to identify a plurality of snippets of information in the at least one unstructured medical record associated with the patient attribute, each snippet including a portion of text extracted from the at least one unstructured medical record;
  tokenize each one of the plurality of snippets to split the portion of text of each one of the plurality of snippets into one or more identified tokens, each of the one or more identified tokens representing an instance of a target term associated with the patient attribute within the plurality of snippets;

convert each of the one or more identified tokens to a word embedding, the word embedding comprising a predetermined value associated with each of the one or more identified tokens;

using the word embedding, generate a snippet vector comprising a plurality of snippet vector elements, the plurality of snippet vector elements comprising weight values associated with at least one word included in the snippet;

analyze the snippet vectors to generate a summary vector comprising a plurality of summary vector elements, wherein each of the plurality of summary vector elements is associated with a corresponding snippet vector element and is determined based on an analysis of the corresponding snippet vector element; and generate, based on the summary vector, at least one output indicative of a probability associated with the patient attribute.

2. The model-assisted system of claim 1, wherein identifying the plurality of snippets comprises searching the at least one unstructured medical record for a keyword associated with the patient attribute.

3. The model-assisted system of claim 2, wherein the keyword comprises at least one variable element.

4. The model-assisted system of claim 3, wherein the variable element is represented as a regular expression.

5. The model-assisted system of claim 1, wherein the snippet vectors are generated using a neural network.

6. The model-assisted system of claim 5, wherein the neural network includes a long short-term memory network.

7. The model-assisted system of claim 1, wherein each summary vector element comprises a maximum of corresponding snippet vector elements in a plurality of snippet vectors.

8. The model-assisted system of claim 1, wherein the probability comprises a probability of whether the patient has been tested for PDL1.

9. The model-assisted system of claim 1, wherein the probability comprises a probability of whether the patient has tested positive for PDL1.

10. The model-assisted system of claim 1, wherein the probability comprises a probability of whether the patient has a history of smoking.

11. The model-assisted system of claim 1, wherein the output includes an indication that an association between the patient and the patient attribute is indeterminate.

12. The model-assisted system of claim 1, wherein the probability comprises a probability of whether a test has been performed on the patient associated with the patient attribute.

13. The model-assisted system of claim 1, wherein the probability comprises a probability of whether the patient has tested positive for the patient attribute.

14. A computer-assisted method for determining probabilities associated with a patient attribute, the system comprising:

accessing a database storing at least one unstructured medical record;

analyzing the at least one unstructured medical record to identify a plurality of snippets of information in the at least one unstructured medical record associated with the patient attribute, each snippet including a portion of text extracted from the at least one unstructured medical record;

tokenizing each one of the plurality of snippets to split the portion of text of each one of the plurality of snippets into one or more identified tokens, each of the one or more identified tokens representing an instance of a target term associated with the patient attribute within the plurality of snippets;

converting each of the one or more identified tokens to a word embedding, the word embedding comprising a predetermined value associated with each of the one or more identified tokens;

using the word embedding, generating a snippet vector comprising a plurality of snippet vector elements, the plurality of snippet vector elements comprising weight values associated with at least one word included in the snippet;

analyzing the snippet vectors to generate a summary vector comprising a plurality of summary vector elements, wherein each of the plurality of summary vector elements is associated with a corresponding snippet vector element and is determined based on an analysis of the corresponding snippet vector element; and generating, based on the summary vector, at least one output indicative of a probability associated with the attribute.

15. The computer-assisted method of claim 14, wherein identifying the plurality of snippets comprises searching the at least one unstructured medical record for a keyword associated with the patient attribute.

16. The computer-assisted method of claim 15, wherein the keyword comprises at least one variable element.

17. The computer-assisted method of claim 16, wherein the variable element is represented as a regular expression.

18. The computer-assisted method of claim 14, wherein the snippet vectors are generated using a neural network.

19. The computer-assisted method of claim 18, wherein the neural network includes a long short-term memory network.

20. The computer-assisted method of claim 14, wherein each summary vector element comprises a maximum of corresponding snippet vector elements in a plurality of snippet vectors.

21. The computer-assisted method of claim 14, wherein the probability comprises a probability of whether the patient has been tested for PDL1.

22. The computer-assisted method of claim 14, wherein the probability comprises a probability of whether the patient has tested positive for PDL1.

23. The computer-assisted method of claim 14, wherein the probability comprises a probability of whether the patient has a history of smoking.

24. The computer-assisted method of claim 14, wherein the output includes an indication that an association between the patient and the patient attribute is indeterminate.

25. The model-assisted system of claim 14, wherein the probability comprises a probability of whether a test has been performed on the patient associated with the patient attribute.

26. The model-assisted system of claim 14, wherein the probability comprises a probability of whether the patient has tested positive for the patient attribute.

* * * * *